United States Patent [19]
Mori et al.

[11] Patent Number: 5,312,978
[45] Date of Patent: May 17, 1994

[54] PROCESS FOR PRODUCING VITAMIN A ACID

[75] Inventors: Toshiki Mori; Hiroshi Fujii; Takashi Onishi, all of Kurashiki; Yoshin Tamai, Shibata, all of Japan

[73] Assignee: Kuraray Company Ltd., Kurashiki, Japan

[21] Appl. No.: 34,910

[22] Filed: Mar. 19, 1993

[30] Foreign Application Priority Data

Mar. 27, 1992 [JP] Japan .................................. 4-101863

[51] Int. Cl.$^5$ .............................................. C07C 51/29
[52] U.S. Cl. ..................................................... 562/510
[58] Field of Search .................................... 562/510, 599

[56] References Cited

U.S. PATENT DOCUMENTS

| | | | |
|---|---|---|---|
| 2,744,928 | 5/1956 | Smith et al. | 562/510 |
| 2,881,212 | 4/1959 | Idol et al. | 562/510 |
| 3,420,880 | 1/1969 | Clark et al. | 562/510 |
| 4,990,662 | 2/1991 | Hagen et al. | 562/510 |

FOREIGN PATENT DOCUMENTS

0292350 11/1988 European Pat. Off. .

OTHER PUBLICATIONS

Boyle et al., Bull. Soc. Chim. Fri, vol. 1990, pp. 565–567, (1990).
Kanehira et al., Chem. Abst., vol. 108, #150,755n (1988).
Tiang et al., Chem. Abst., vol. 115, #8205; (1991).
Dalcanale et al., Chem. Abst., vol. 103, #214,990s (1985).
Tetrahedron, vol. 37, No. 11, 1981, pp. 2091–2096, B. S. Bal, et al., "Oxidation of Alpha, Beta-Unsaturated Aldehydes".
Patent Abstracts of Japan, vol. 17, No. 37, (C–1019) 1992, JP-A-42 53 934.

*Primary Examiner*—James H. Reamer
*Attorney, Agent, or Firm*—Oblon, Spivak, McClelland Maier & Neustadt

[57] ABSTRACT

A process for producing vitamin A acid, having useful biological activity, which comprises oxidizing vitamin A aldehyde with an aqueous solution of an alkali metal chlorite in the presence of an acid.

10 Claims, No Drawings

PROCESS FOR PRODUCING VITAMIN A ACID

BACKGROUND OF THE INVENTION

1. Field of the Invention

The present invention relates to a process for producing vitamin A acid from vitamin A aldehyde.

2. Description of the Related Art

Vitamin A acid is known to possess the function of curing various diseases and lesions, for example those caused by deficiency of vitamin A. Thus, there has been suggested possibility of vitamin A acid being usable as a therapeutic agent for deficiency of vitamin A and like symptoms.

Many processes are known to produce vitamin A acid (see for example "The Retinoides, Volume 1, Michael B. S. et al., Academic Press"). Among those processes, one that performs the production in the shortest procedure comprises using, as starting material, vitamin A acetate, which is being produced on an industrial scale in a large amount and is readily available, converting it via vitamin A to vitamin A aldehyde and then oxidizing the aldehyde. Vitamin A can readily be obtained by hydrolyzing vitamin A acetate under the usual alkaline condition. A known process for producing vitamin A aldehyde from vitamin A is the Oppenauer oxidation using tertiary aldehyde (Japanese Patent Application Laid-open No. 206076/1991). A known process for converting vitamin A aldehyde or its analogues to vitamin A acid structure comprises oxidizing the former with a catalyst of manganese oxide, manganese oxide and sodium cyanide, silver oxide or the like (see for example Kaneko, R. et al., Chem. Ind. (London) 1971, (36), 1016, and Barua, R. K., Curr. Sci. 37, 364 (1968)). This process for producing vitamin A acid however uses an expensive and toxic heavy metal compound such as manganese or silver and is hence rarely employed on an industrial scale in practice.

SUMMARY OF THE INVENTION

Accordingly, an object of the Present invention is to solve the above problems associated with the prior art and to provide a process for producing, in one step, vitamin A acid by using as starting material vitamin A aldehyde that is readily derivable from vitamin A acetate, which is being commercially produced on a large scale, at a low cost and high yield and without using toxic heavy metal compounds, such as manganese and silver.

The above object can be achieved, according to the present invention, by oxidizing vitamin A aldehyde with an aqueous solution of an alkali metal chlorite in the presence of an acid.

DETAILED DESCRIPTION OF THE INVENTION

Alkali metal salts of chlorous acid are used as oxidizing agents in the present invention. Examples of the alkali metal chlorites are sodium chlorite and potassium chlorite, in the form of powder or aqueous solution, and they are commercially available. Aqueous solutions of alkali metal chlorites can be used as they are, while those in the powder form are dissolved in water and subjected to reaction. The aqueous alkali metal chlorite solution used preferably has a concentration of 0.1 to 50% by weight, more preferably 15 to 30% by weight. The alkali metal chlorite is used in an amount of at least one molar equivalent relative to vitamin A aldehyde, more preferably in a range of 1 to 1.8 molar equivalents.

In the present invention, an acid is used in addition to the aqueous alkali metal chlorite solution. The acid is used for the purpose of reacting with the alkali metal chlorite, thereby generating unstable chlorous acid. Examples of the acid are inorganic acids such as hydrochloric acid, sulfuric acid and phosphoric acid; what is known as acidic inorganic salts, such as sodium dihydrogenphosphate and potassium dihydrogenphosphate; and organic acids such as acetic acid and propionic acid. In view of reaction results and economy, inorganic acids such as sulfuric acid and phosphoric acid are preferred among these acids, and phosphoric acid is particularly preferred. These acids are used as they are or in the form of aqueous solutions.

The acids are used in at least equimolar amount relative to the alkali metal chlorite, particularly in a range of 1 to 6 molar equivalents for practical purposes.

The reaction according to the present invention is effected by adding an acid to a mixture containing vitamin A aldehyde and an alkali metal chlorite. Since addition of an acid generates heat of reaction, it is important to add the acid dropwise, gradually, so that the designated reaction temperature can be maintained.

The reaction is generally conducted at a temperature in a range of 0° to 100° C. In view of stability of the starting material vitamin A aldehyde and product vitamin A acid and the like, the reaction temperature is more Preferably in a range of 0° to 20.C.

Although it is difficult to specify the reaction time, which varies depending on the reaction conditions employed, the reaction is generally completed within 3 hours.

In the present invention, it is recommended to use, in addition to the above-mentioned alkali metal chlorite and acid, a lower unsaturated compound having at least one double bond and at least 3 carbon atoms, in particular about 4 to 10 carbon atoms. This lower unsaturated compound has the function of catching hypochlorous acid and the like that form as by-products during the reaction.

Examples of usable lower unsaturated compounds are propene, 1-butene, 2-butene, isobutene, 3-methyl-1-butene, 2-methyl-2-butene, isoprene, 1-hexene, 2-hexene, 2,6-dimethyl-2,6-octadiene and myrcene. Among these compounds, 2-methyl-2-butene is preferred because it is inexpensive and that its boiling point falls within a range assuring easy handling.

There is no particular limitation to the amount of these lower unsaturated compounds, but it is generally in a range of 0.1 to 100 times the weight of vitamin A aldehyde. In view of economy and the like, it is recommended to use a lower unsaturated compound in an amount of 3 to 6 times the weight of vitamin A aldehyde.

In the present invention, an organic solvent is used to dissolve the starting material vitamin A aldehyde. It is necessary that the organic solvent dissolve vitamin A aldehyde and do not inhibit its oxidation. Examples of the organic solvent that satisfies these conditions are cyclic and straight chain ethers such as dioxane, tetrahydrofuran, ethyl ether and isopropyl ether; aromatic and aliphatic hydrocarbons such as toluene, hexane and heptane; halohydrocarbons such as methylene chloride, chloroform and dichloroethane. Dioxane, which can mixes with both water and organic substances, gives Particularly good reaction results. The organic solvent is used preferably in an amount of at least 0.1 times, more preferably 0.5 to 5 times the volume of vitamin A aldehyde.

It is important, in view of stability of the starting material vitamin A aldehyde and reaction product vitamin A acid, that these compounds be not exposed to light to an extent more than necessary during oxidation, the succeeding extraction or like operations. It is desirable that these oxidation, extraction and like operations be conducted under an atmosphere of an inert gas such as nitrogen, helium or argon.

In the present invention, completion of the oxidation is confirmed by checking exhaustion of vitamin A aldehyde, which can readily be Performed by thin layer chromatography or liquid chromatography.

After completion of the oxidation, vitamin A acid can be extracted from the reaction mixture with an extraction solvent of toluene, ethyl acetate or methylene chloride. The organic layer extracted is washed and the solvent is removed under reduced pressure, to isolate vitamin A acid as the residue. Where oxidation is conducted with a reaction solvent of dioxane, there precipitates during the reaction vitamin A acid, which can, after completion of the reaction, be withdrawn by filtration.

The crude vitamin A acid thus obtained can be purified by dissolution in an alkaline condition utilizing potassium hydroxide or the like and the succeeding precipitation with an acid such as sulfuric acid. The vitamin A acid thus purified can further be purified by crystallization from a solvent such as ethanol or by silica gel chromatography, to give high-purity vitamin A acid.

Vitamin A aldehyde, which is used as the starting material in the present invention, can be obtained as follows. Vitamin A, which is obtained by hydrolysis of vitamin A acetate, is reacted with a tertiary aldehyde such as trimethylacetaldehyde or 2,2 dimethyl-4-pentenal in the presence of a catalytic amount of an aluminum alkoxide (see Japanese Patent Application Laid-open No. 206076/1991). The vitamin A aldehyde obtained by this process can, without being purified or, if necessary, after being purified by crystallization or the like, be used as the starting material in the present invention.

The process of the present invention thus readily gives vitamin A acid from vitamin A aldehyde. Furthermore, the process of the present invention is applicable to conversion of aliphatic polyene aldehydes having conjugated double bonds, such as vitamin A aldehyde, to corresponding aliphatic polyene acids. In this case, these polyene aldehydes may have various substituents insofar as they do not participate in the reaction.

EXAMPLES

Other features of the invention will become apparent in the course of the following descriptions of exemplary embodiments which are given for illustration of the invention and are not intended to be limiting thereof.

Example 1

Synthesis of vitamin A acid (all trans form)

A 1-liter three-necked flask was charged under an atmosphere of nitrogen with 54.9 g of vitamin A aldehyde (69.1% purity, 133.6 mmoles, ratio of all trans form: 98.5%), 250 g of 2-methyl-2-butene, 100 ml of dioxane and 53.2 g of a 25% aqueous sodium chlorite solution. The mixture was mechanically stirred vigorously and, while the internal temperature was maintained at 5° C., 170 g of a 8.5% aqueous phosphoric acid solution was added thereto dropwise over 1.5 hours. After completion of the addition, the mixture was further stirred vigorously at 5° C. for 40 minutes. After confirming exhaustion of the starting material vitamin A aldehyde by thin layer chromatography, yellow solid that precipitated was filtered through a glass filter and then washed several times with water. The yellow solid was transferred to a 500-ml flask, and 200 ml of a 5% aqueous potassium hydroxide solution and 100 ml of ethanol were added thereto. The mixture was refluxed with heating for 1.5 hours. After cooling, the reaction mixture was transferred to a 1-liter separating funnel. To the mixture 200 ml of hexane was added and the funnel was shaken sufficiently. The bottom layer was separated and acidified with a 10% aqueous sulfuric acid solution. The yellow solid that precipitated was extracted with 500 ml of isopropyl ether and the extract was washed with water until the bottom layer became neutral. The isopropyl ether was distilled off under reduced pressure and 400 ml of ethanol was added to the yellow residue and the mixture was heated. After confirmation of complete dissolution, the solution was gradually cooled with stirring to 0° C. The vitamin A acid crystal that precipitated was filtered through a glass filter and then washed with cold ethanol. The crystal was dried under reduced pressure, to give 22.3 g of vitamin A acid having a purity of at least 99%. The yield was 55.9%. The vitamin A acid thus obtained had a all trans form ratio of 99.5%.

Example 2

Synthesis of vitamin A acid (13-cis form)

A 200-ml three-necked flask was charged under an atmosphere of nitrogen with 8.86 g of vitamin A aldehyde (80.1% purity, 25 mmoles, ratio of 13-cis form: 92%), 50 g of 2-methyl-2-butene, 20 ml of dioxane and 10 g of a 25% aqueous sodium chlorite solution, and the mixture was mechanically stirred vigorously. Then, 32 g of an aqueous phosphoric acid solution was added dropwise thereto, while the internal temperature was maintained at 5° C., over 15 minutes. Vigorous stirring was continued at 5° C. for further 40 minutes. Confirmation of completion of the reaction and after-treatment were conducted in the same manner as in Example 1, to obtain 3.46 g of vitamin A acid with a purity of at least 99%. The yield was 46%. The vitamin A acid thus obtained had a 13-cis form ratio of 95%.

Reference Example

Synthesis of vitamin A aldehyde from vitamin A acetate

A 500-ml three-necked flask was charged under an atmosphere of nitrogen with 205 g of methanol, 50.2 g of vitamin A acetate (98% purity, 150 mmoles, ratio of all trans form: 98.6%), 24 g of a 50% aqueous sodium hydroxide solution, and the mixture was mechanically stirred at room temperature for 1 hour. The contents were transferred to a 1-liter separating funnel. To the contents 150 ml of hexane and 200 g of water were added and, after sufficient shaking, the mixture was separated. The organic layer separated was washed several times with water and the hexane was distilled off under reduced pressure, to obtain 47.06 g of a crude vitamin A.

The crude substance was, under an atmosphere of nitrogen, transferred to a 200-ml three-necked flask and 26 g (300 mmoles) of trimethylacetaldehyde was added and then 1.16 g of aluminum isopropoxide. The contents was mechanically stirred at 45° to 50° C. for 50 minutes. To the contents 1 ml of water was added to terminate reaction and 100 ml of hexane was added. The reaction mixture was subjected to distillation under reduced Pressure to remove low boiling substances such as hexane and trimethylacetaldehyde, to give 54.9 g of vitamin A aldehyde with a purity of 69.1%. The yield was 89.7%. The vitamin A aldehyde thus obtained had a all trans form ratio of 98.5%.

The vitamin A aldehyde thus obtained was used as it is as a starting material in Example 1.

Obviously, numerous modifications and variations of the present invention are possible in light of the above teachings. It is therefore to be understood that within the scope of the appended claims, the invention may be practiced otherwise than as specifically described herein.

What is claimed is:

1. A process for producing vitamin A acid which comprises oxidizing vitamin A aldehyde by gradually dropwise adding an acid to a mixture comprising vitamin A aldehyde, an aqueous solution of an alkali metal chlorite and a lower unsaturated compound having at least one double bond and at least 3 carbon atoms.

2. A process according to claim 1, wherein said alkali metal is sodium or potassium.

3. A process according to claim 1, wherein said alkali metal chlorite is used in an amount of at least one molar equivalent relative to vitamin A aldehyde.

4. A process according to claim 1, wherein said acid is an organic acid, an acidic inorganic salt or an inorganic acid.

5. A process according to claim 4, wherein said acid is phosphoric acid.

6. A process according to claim 1, wherein said acid is used in an amount of at least one molar equivalent relative to vitamin A aldehyde.

7. A process according to claim 1, wherein the oxidation is effected in an organic solvent selected from the group consisting of cyclic and straight chain ethers, aromatic and aliphatic hydrocarbons and halohydrocarbons.

8. A process according to claim 7, wherein said organic solvent is dioxane.

9. A process according to claim 1, wherein said lower unsaturated compound was selected from a group consisting of propene, 1-butene, 2-butene, isobutene, 3-methyl-1-butene, 2-methyl-2-butene, isoprene, 1-hexene, 2-hexene, 2,6-dimethyl-2,6-octadiene and myrcene.

10. A process according to claim 1, wherein the oxidation is effected at a temperature in a range of from 0° to 100° C.

* * * * *